United States Patent (12)
Wang et al.

(10) Patent No.: US 12,215,153 B1
(45) Date of Patent: Feb. 4, 2025

(54) ANTI-RECEPTOR EXPRESSED ON LYMPHOID TISSUES (RELT) RECOMBINANT MONOCLONAL ANTIBODY AND PREPARATION METHOD AND USE THEREOF

(71) Applicant: TONGJI HOSPITAL, TONGJI MEDICAL COLLEGE OF HUST, Wuhan (CN)

(72) Inventors: Congyi Wang, Wuhan (CN); Shanjie Rong, Wuhan (CN); Fei Sun, Wuhan (CN); Chunliang Yang, Wuhan (CN); Jiahui Luo, Wuhan (CN)

(73) Assignee: TONGJI HOSPITAL, TONGJI MEDICAL COLLEGE OF HUST, Wuhan (CN)

( * ) Notice: Subject to any disclaimer, the term of this patent is extended or adjusted under 35 U.S.C. 154(b) by 0 days.

(21) Appl. No.: 18/745,750

(22) Filed: Jun. 17, 2024

(30) Foreign Application Priority Data

Aug. 30, 2023 (CN) .......................... 202311101875.6

(51) Int. Cl.
| | |
|---|---|
| C07K 16/00 | (2006.01) |
| A61P 3/10 | (2006.01) |
| C07K 16/28 | (2006.01) |
| C07K 16/46 | (2006.01) |
| A61K 39/00 | (2006.01) |

(52) U.S. Cl.
CPC ............ *C07K 16/2803* (2013.01); *A61P 3/10* (2018.01); *A61K 2039/505* (2013.01); *C07K 2317/14* (2013.01); *C07K 2317/76* (2013.01)

(58) Field of Classification Search
None
See application file for complete search history.

(56) References Cited

U.S. PATENT DOCUMENTS

2018/0177808 A1    6/2018    Zebala et al.

FOREIGN PATENT DOCUMENTS

| CN | 101432306 A | 5/2009 |
|---|---|---|
| CN | 108473552 A | 8/2018 |
| WO | 2007117763 A2 | 10/2007 |
| WO | 2010110838 A2 | 9/2010 |
| WO | 2021067628 A2 | 4/2021 |

OTHER PUBLICATIONS

"Implementation Rules for the Management of Medical Experimental Animals," Ministry of Health, Jan. 25, 1998, 11 pages.
Jiping, "Fundamentals of Molecular Biology," People's Health Publishing House, ISBN7-117-03914-0/R, Nov. 30, 2000, 13 pages.
Ming et al., "Application of Tumor-Associated Antigen and Antibody Detection in the Diagnosis of Malignant Tumors," Chin Med Biotechnol, Oct. 2013, vol. 8, No. 5, pp. 376-382.
Zhang et al., "ELISA Based Serum Glial Fibnillary Acidic Protein Autoantibody Detection and its Application in Glioblastoma Diagnosis," Journal of Fudan University (Medical Edition), Nov. 2011, vol. 38, No. 6, pp. 538-542.

*Primary Examiner* — Maher M Haddad

(57) ABSTRACT

The present disclosure relates to the technical field of chemoimmunology, and in particular to an anti-receptor expressed on lymphoid tissues (RELT) recombinant monoclonal antibody and a preparation method and use thereof. The anti-RELT recombinant monoclonal antibody includes a heavy chain variable region and a light chain variable region, where the amino acid sequence of the heavy chain variable region is set forth in SEQ ID NO: 4; the amino acid sequence of the light chain variable region is set forth in SEQ ID NO: 5; and the anti-RELT recombinant monoclonal antibody has a biological activity of neutralizing a function of RELT. In addition, because the anti-RELT recombinant monoclonal antibody has the biological activity of neutralizing the function of RELT, the anti-RELT recombinant monoclonal antibody can specifically recognize and detect the expression of RELT in different tissues and cells.

2 Claims, 7 Drawing Sheets

Specification includes a Sequence Listing.

SEQUENCE LISTING

```
Sequence total quantity: 9
SEQ ID NO: 1            moltype = AA  length = 138
FEATURE                 Location/Qualifiers
source                  1..138
                        mol_type = protein
                        note = Amino acid sequence of a polypeptide
                        organism = synthetic construct
SEQUENCE: 1
PTPITPWLCP PGKEPDPDPG QGTLCRTCPP GTFSASWNSY PCQPHYRCSL QKRLEAQAGT   60
ATHDTMCGDC QHGWFGPQGV PHVPCQPCSK APPSTGGCDE SGRRGRRGVE VAAGTSSNGE  120
PRQPGNGTRA GGPEETAA                                                138

SEQ ID NO: 2            moltype = DNA  length = 1380
FEATURE                 Location/Qualifiers
source                  1..1380
                        mol_type = other DNA
                        note = DNA sequence encoding a heavy chain variable region
                         of an anti-RELT recombinant rabbit monoclonal antibody
                         E19399-5B2
                        organism = synthetic construct
SEQUENCE: 2
atggagactg ggctgcgctg gcttctcctg gtcgctgtac tcagaggtgt ccagtgtcag   60
tcggtgaagg agtccggggg aggcctcttc aagccaacgg atacccctgac actcacctgc  120
acagtctctg gattctccct cagtacctat gcaatgtcct gggtccgcca gactccaggg  180
attgggctgg agtggatcgg gatcgttaat gttgctggtg atacagccta cgcgagctgg  240
```

```
gcgatgagcc gatccaccat caccagaaac accaacgaca acacggtgac tctgaaaatg   300
accagtctga cagccgcgga cacggccacc tatttctgta cacgacatgg tgagaatatt   360
ggtgacatgt ggggcccagg caccctgatt gccgtctcct cagtgcctgc aaccccccg    420
atcatcttcc cgctgacctg ccccggggtgt gtactgaaag acacttcagc gaccattgtc  480
gccggctgcc tggtcaaagg ctacctcccg gagccagtga ccgtgacctg gaactcgggc   540
accctcacca atggggtacg caccttcccg tccgtccggc agtcctcagg cctctactcg   600
ctgagcagcg tggtgagcgt gacctcaagc agccagcccg tcacctgcaa cgtggcccac   660
ccagccacca acaccaaagt ggacaagacc gttgcgccct cgacatgcag caagcccatg   720
tgcccacccc ctgaactccc gggggggaccg tctgtcttca tcttcccccc aaaacccaag   780
gacacccctca tgatctcacg cacccccgag gtcacatgcg tggtggtgga cgtgagccag   840
gatgaccccg aggtgcagtt cacatggtac ataaacaacg agcaggtgcg caccgcccgg   900
ccgccgctac gggagcagca gttcaacagc acgatccgcg tggtcagcac cctccccatc   960
gcgcaccagg actggctgag gggcaaggag ttcaagtgca aagtccacaa caaggcactc  1020
ccggccccca tcgagaaaac catctccaaa gccagaggc agccccctgga gccccggaaggtc  1080
tacaccatgg gccctccccg ggaggagctg agcagcaggt cggtcagcct gacctgcatg  1140
atcaacggct ctaccccttc cgacatctcg gtggagtggg agaagaacgg gaaggcagag  1200
gacaactaca agaccacgcc gaccgtgctg gacagcgacg gctcctactt cctctacagc  1260
aagctctcag tgcccacgag tgagtggcag cggggcgatg tcttcacctg ctcgtgatg   1320
cacgaggcct tgcacaacca ctacacgcag aagtccatct cccgctctcc gggtaaatag  1380

SEQ ID NO: 3            moltype = DNA  length = 711
FEATURE                 Location/Qualifiers
source                  1..711
                        mol_type = other DNA
                        note = DNA sequence encoding a light chain variable region
                         of the anti-RELT recombinant rabbit monoclonal antibody
                        organism = synthetic construct
SEQUENCE: 3
atggacacga gggcccccac tcagctgctg gggctcctgc tgctctggct cccaggtgcc   60
atctgtgacc ctgtgatgac ccagactcca tcttccacgt ctgcggctgt gggaggcaca  120
gtcaccatca attgccaggc cagtcagagt gtttatgcta acaactactt atcctgtttt  180
cagaagaaac caggacagcc tcccaagcaa ctgatctatg atgcatccac tctggcatct  240
ggggtcccat cgcggttcaa aggcagtgga tctgggacac agttcactct caccatcagc  300
ggcgtgcagt gtgacgatgc tgccgcctac tattgtgcag gcggttttac tggtgcgatt  360
tttccttttcg gcggagggac cgaggtggtg gtcaaaggta atccagttgc acctactgtc  420
ctcatcttcc caccagctgc tgatcaggtg gcaactggaa cagtcaccat cgtgtgtgtg  480
gcgaataaat actttcccga tgtcaccgtc acctgggagg tggatggcac cacccaaaca  540
actggcatcg agaacagtaa aacaccgcag aattctgcag attgtaccta acctcagc    600
agcactctga cactgaccag cacacagtac aacgccaca aagagtacac ctgcaaggtg   660
acccagggca cgacctcagt cgtccagagc ttcaataggg gtgactgtta g           711

SEQ ID NO: 4            moltype = AA  length = 459
FEATURE                 Location/Qualifiers
source                  1..459
                        mol_type = protein
                        note = An amino acid sequence of the heavy chain variable
                         region of the anti-RELT recombinant monoclonal antibody
                         E19399-5B2
                        organism = synthetic construct
SEQUENCE: 4
METGLRWLLL VAVLRGVQCQ SVKESGGGLF KPTDTLTLTC TVSGFSLSTY AMSWVRQTPG   60
IGLEWIGIVN VAGDTAYASW AMSRSTITRN TNDNTVTLKM TSLTAADTAT YFCTRHGENI  120
GDMWGPGTLI AVSSVPATPP IIFPLTCPGC VLKDTSATIV AGCLVKGYLP EPVTVTWNSG  180
TLTNGVRTFP SVRQSSGLYS LSSVVSVTSS SQPVTCNVAH PATNTKVDKT VAPSTCSKPM  240
CPPPELPGGP SVFIFPPKPK DTLMISRTPE VTCVVVDVSQ DDPEVQFTWY INNEQVRTAR  300
PPLREQQFNS TIRVVSTLPI AHQDWLRGKE FKCKVHNKAL PAPIEKTISK ARGQPLEPKV  360
YTMGPPREEL SSRSVSLTCM INGFYPSDIS VEWEKNGKAE DNYKTTPTVL DSDGSYFLYS  420
KLSVPTSEWQ RGDVFTCSVM HEALHNHYTQ KSISRSPGK                         459

SEQ ID NO: 5            moltype = AA  length = 176
FEATURE                 Location/Qualifiers
source                  1..176
                        mol_type = protein
                        note = An amino acid sequence of the light chain variable
                         region of the anti-RELT recombinant monoclonal antibody
                         E19399-5B2
                        organism = synthetic construct
SEQUENCE: 5
MDTRAPTQLL GLLLLWLPGA ICDPVMTQTP SSTSAAVGGT VTINCQASQS VYANNYLSWF   60
QKKPGQPPKQ LIYDASTLAS GVPSRFKGSG SGTQFTLTIS GVQCDDAAAY YCAGGFTGAI  120
FPFGGGTEVV VKGDPVAPTV LIFPPAADQV ATGTVTIVCV ANKYFPDVTV TWEVDG      176

SEQ ID NO: 6            moltype = DNA  length = 21
FEATURE                 Location/Qualifiers
source                  1..21
                        mol_type = other DNA
                        note = Primer VH-F
                        organism = synthetic construct
SEQUENCE: 6
```

```
agactgggct gcgctggctt c                                              21

SEQ ID NO: 7            moltype = DNA  length = 15
FEATURE                 Location/Qualifiers
source                  1..15
                        mol_type = other DNA
                        note = Primer VH-R
                        organism = synthetic construct
SEQUENCE: 7
gtgagggtgc ccgag                                                     15

SEQ ID NO: 8            moltype = DNA  length = 22
FEATURE                 Location/Qualifiers
source                  1..22
                        mol_type = other DNA
                        note = Primer VK-F
                        organism = synthetic construct
SEQUENCE: 8
atggacayga gggcccccac tc                                             22

SEQ ID NO: 9            moltype = DNA  length = 23
FEATURE                 Location/Qualifiers
source                  1..23
                        mol_type = other DNA
                        note = Primer VK-R
                        organism = synthetic construct
SEQUENCE: 9
ggtgggaaga tgaggacagt agg                                            23
```

ANTI-RECEPTOR EXPRESSED ON LYMPHOID TISSUES (RELT) RECOMBINANT MONOCLONAL ANTIBODY AND PREPARATION METHOD AND USE THEREOF

CROSS-REFERENCE TO RELATED APPLICATION

This patent application claims the benefit and priority of Chinese Patent Application No. 202311101875.6 filed with the China National Intellectual Property Administration on Aug. 30, 2023, the disclosure of which is incorporated by reference herein in its entirety as part of the present application.

REFERENCE TO SEQUENCE LISTING

A computer readable XML file entitled "GWP20240201170", that was created on Apr. 11, 2024, with a file size of about 13,611 bytes, contains the sequence listing for this application, has been filed with this application, and is hereby incorporated by reference in its entirety.

TECHNICAL FIELD

The present application relates to the technical field of chemoimmunology, and in particular to an anti-receptor expressed on lymphoid tissues (RELT) recombinant monoclonal antibody and a preparation method and use thereof.

BACKGROUND

Receptor expressed on lymphoid tissues (RELT) is a membrane receptor protein with a molecular weight of 43 kDa. RELT belongs to the tumor necrosis factor receptor superfamily (TNFRSF), and is also known as TNFRSF19L. An extracellular segment of RELT includes three conserved cysteine-rich domains, and an intracellular segment of RELT lacks a death domain. Therefore, RELT is a non-death receptor. Like other members of the TNFRSF, RELT exists in both a membrane-bound form and a free form. The transformation of RELT from a membrane-bound form to a free form is allowed in a manner of ectodomain shedding. During ectodomain shedding, an amino acid at position 137 of an extracellular membrane-proximal part of RELT can be released through cleavage, such that RELT becomes soluble RELT (sRELT). The ectodomain shedding is mediated by members of matrix metalloprotease and disintegrin families, such as ADAM17, ADAM9, ADAM10, ADAM19, MMP7, Elastase, and Proteinase 3. RELT is highly expressed in immune cells such as T cells and dendritic cells (DCs), and is closely related to the activation of an immune system. In addition, existing studies have shown that a free sRELT level in serum of a tumor patient is significantly increased, indicating that RELT may be a potential early diagnosis marker for a tumor. Therefore, RELT is expected to be a new target for intervention of autoimmune diseases and immune-associated diseases such as tumors.

Ligands and downstream signaling pathways corresponding to 28 members of the TNFRSF except for RELT have been identified. However, the anti-RELT antibodies currently on the market have disadvantages such as low potency ratio and poor specificity, and can hardly meet the needs of RELT protein detection at a cell level and a tissue level. For example, in practical applications, an anti-RELT antibody product (MAB1385) exhibits poor specificity due to a design of an antigen polypeptide sequence for inducing an anti-RELT protein polyclonal antibody, and has the defect of causing many impurity bands during detection. Therefore, how to provide a high-quality, reliable, and accurate anti-RELT recombinant monoclonal antibody is a technical problem that needs to be solved urgently.

SUMMARY

The present disclosure provides an anti-RELT recombinant monoclonal antibody and a preparation method and use thereof to solve the technical problem that the anti-RELT antibodies in the prior art have a low potency ratio and poor specificity.

In a first aspect, the present disclosure provides an anti-RELT recombinant monoclonal antibody, including a heavy chain variable region and a light chain variable region, where an amino acid sequence of the heavy chain variable region is set forth in SEQ ID NO: 4; an amino acid sequence of the light chain variable region is set forth in SEQ ID NO: 5; and the anti-RELT recombinant monoclonal antibody has a biological activity of neutralizing a function of RELT.

Optionally, the anti-RELT recombinant monoclonal antibody is obtained by immunizing a lymphocyte with a specific antigen, and an amino acid sequence of the specific antigen is set forth in SEQ ID NO: 1.

In a second aspect, the present disclosure provides a coding gene, including a genome encoding the anti-RELT recombinant monoclonal antibody described in the first aspect, where the genome includes a first gene fragment encoding the heavy chain variable region and a second gene fragment encoding the light chain variable region; and a nucleotide sequence of the first gene fragment is set forth in SEQ ID NO: 2 and a nucleotide sequence of the second gene fragment is set forth in SEQ ID NO: 3.

In a third aspect, the present disclosure provides a nucleic acid including the coding gene described in the second aspect.

In a fourth aspect, the present disclosure provides a recombinant expression vector including the nucleic acid described in the third aspect, where the recombinant expression vector includes a recombinant plasmid.

In a fifth aspect, the present disclosure provides a method for preparing the recombinant expression vector described in the fourth aspect, including:
  subjecting the nucleic acid described in the third aspect to polymerase chain reaction (PCR) amplification with a primer set to obtain an amplification product; and
  cloning the amplification product on an expression vector to obtain the recombinant expression vector,
  where the primer set includes a primer pair for the heavy chain variable region and a primer pair for the light chain variable region.

In a sixth aspect, the present disclosure provides a method for preparing the anti-RELT recombinant monoclonal antibody, including:
  transfecting a cell with the recombinant expression vector described in the fourth aspect, and cultivating the cell to obtain a cell culture; and
  collecting a supernatant of the cell culture, and conducting purification to obtain the anti-RELT recombinant monoclonal antibody.

In a seventh aspect, the present disclosure provides an RELT protein detection device, where a biological component of the RELT detection device includes at least one selected from the group consisting of the anti-RELT recombinant monoclonal antibody described in the first aspect, the coding gene described in the second aspect, the nucleic acid described in the third aspect, and the recombinant expression vector described in the fourth aspect, and the RELT detection device includes at least one selected from the group consisting of a test kit, an antibody chip, and an antibody probe.

In an eighth aspect, the present disclosure provides a use of an anti-RELT recombinant monoclonal antibody, including a use of the anti-RELT recombinant monoclonal antibody described in the first aspect in preparation of a therapeutic drug for an autoimmune disease.

Optionally, the autoimmune disease includes at least one selected from the group consisting of type 1 diabetes, rheumatoid arthritis, systemic lupus erythematosus, Sjogren's syndrome, multiple sclerosis, Hashimoto's thyroiditis, primary myxedema, hyperthyroidism, autoimmune hemolytic anemia, ulcerative colitis, atrophic gastritis, and autoimmune glomerulonephritis.

Compared with the prior art, the above technical solutions provided in the embodiments of the present disclosure have the following advantages:

In the anti-RELT recombinant monoclonal antibody provided in the embodiment of the present disclosure, both a heavy chain variable region and a light chain variable region include a binding domain that specifically recognizes and binds to an antigen, an amino acid sequence targeting an RELT antigen is optimized and designed, and amino acid sequences of the heavy chain variable region and the light chain variable region are separately designed accordingly. Therefore, the anti-RELT recombinant monoclonal antibody can bind to RELT protein with high specificity and high sensitivity. In addition, because the anti-RELT recombinant monoclonal antibody has a biological activity of neutralizing a function of RELT, the anti-RELT recombinant monoclonal antibody can specifically recognize and detect the expression of RELT protein on different tissues and cells, and is positively and highly expressed when detecting RELT, which can avoid the defect of causing many impurity bands and is conducive to improving the accuracy and reliability of detection or evaluation.

BRIEF DESCRIPTION OF THE DRAWINGS

The drawings herein are incorporated into the specification and constitute a part of the specification, illustrate embodiments that conform to the present disclosure, and are used together with the specification to explain the principles of the present disclosure.

To describe the technical solutions in the embodiments of the present disclosure or in the prior art clearly, the drawings required for describing the embodiments or the prior art are briefly described below. Apparently, those of ordinary skill in the art may still derive other drawings from these drawings without creative efforts.

DETAILED DESCRIPTION OF THE EMBODIMENTS

In order to make the objectives, technical solutions, and advantages of the embodiments of the present disclosure clear, the technical solutions in the embodiments of the present disclosure are clearly and completely described below with reference to the drawings in the embodiments of the present disclosure. Apparently, the described embodiments are some rather than all of the embodiments of the present disclosure. All other embodiments obtained by those of ordinary skill in the art based on the embodiments of the present disclosure without creative efforts should fall within the protection scope of the present disclosure.

Unless otherwise specified, various raw materials, reagents, instruments, devices, and the like used in the present disclosure can be purchased from the market or can be prepared by the existing methods. The terms "subject", "individual", and "patient" in the present disclosure can be used interchangeably, and refer to vertebrates, in particular mammals. The mammals include, but are not limited to, rodents, monkeys, humans, farm animals, sporting animals, and pets, and further include tissues, cells, and offspring of biological entities obtained in vitro or cultivated in vitro.

Figure 1:
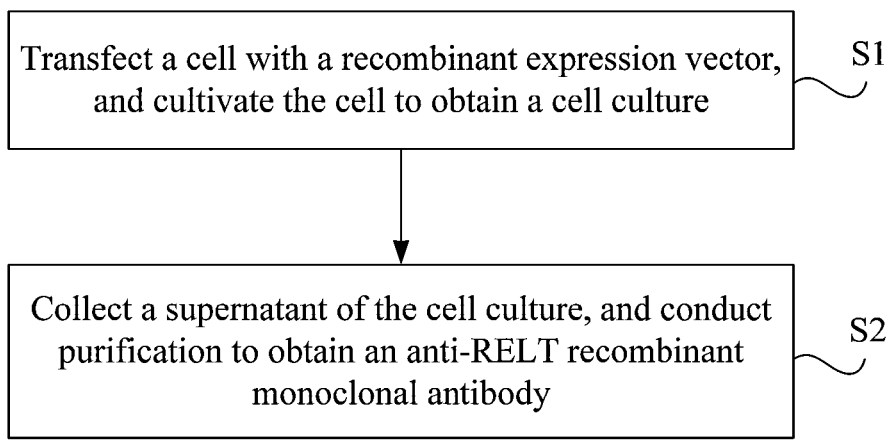
FIG. 1 is a schematic flow chart of a method for preparing an anti-RELT recombinant monoclonal antibody provided in an embodiment of the present disclosure.

As shown in FIG. 1, an embodiment of the present disclosure provides an anti-RELT recombinant monoclonal antibody, including a heavy chain variable region and a light chain variable region, where an amino acid sequence of the heavy chain variable region is set forth in SEQ ID NO: 4; an amino acid sequence of the light chain variable region is set forth in SEQ ID NO: 5; and the anti-RELT recombinant monoclonal antibody has a biological activity of neutralizing a function of RELT.

In the embodiment of the present disclosure, the amino acid sequences of the heavy chain variable region and the light chain variable region of the anti-RELT recombinant monoclonal antibody are designed separately, which can avoid the situation where an antibody finally produced is unstably expressed due to design of a heavy chain variable region or a light chain variable region alone, improve the specificity and sensitivity of the anti-RELT recombinant monoclonal antibody to recognize RELT protein on different tissues and cells, and make the anti-RELT recombinant monoclonal antibody have a biological activity of neutralizing RELT.

It should be noted that, due to high specificity and high sensitivity, the anti-RELT recombinant monoclonal antibody can accurately and reliably detect the expression of RELT protein on different tissues and cells in detection and screening fields such as immunohistochemistry (IHC), indirect ELISA, WB, antibody chip preparation, and flow cytometry.

Due to the above characteristics, the anti-RELT recombinant monoclonal antibody also can recognize recombinant RELT antigen proteins and RELT molecules on different tissues and cells. Therefore, the anti-RELT recombinant monoclonal antibody can also be used in IHC pathological diagnostic agents and ELISAkit mass production.

Alternatively, the anti-RELT recombinant monoclonal antibody is obtained by immunizing a lymphocyte with a specific antigen, and an amino acid sequence of the specific antigen is set forth in SEQ ID NO: 1.

Figure 4:
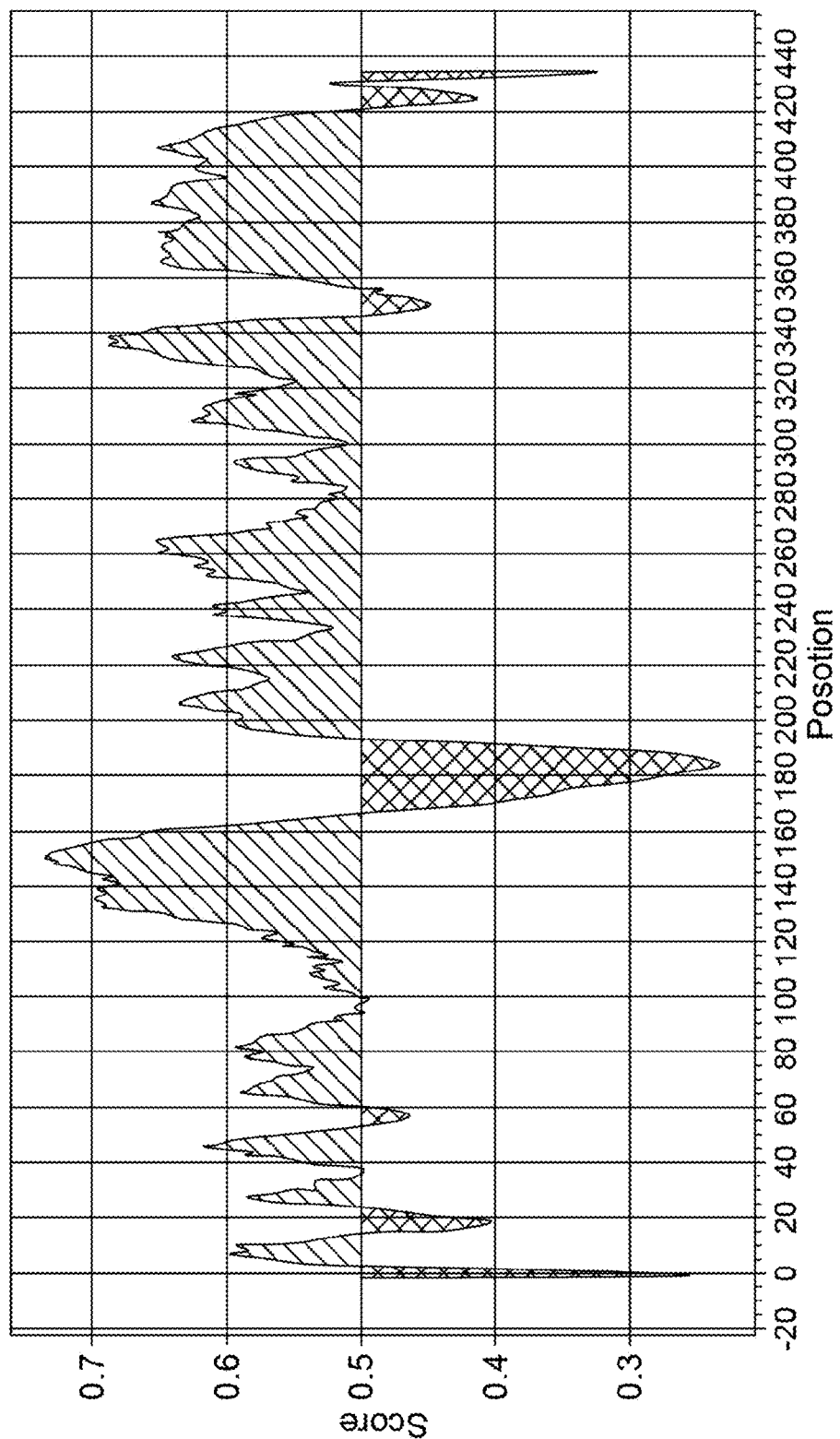
FIG. 4 shows analysis results of antigenicity of an RELT protein provided in an embodiment of the present disclosure.

In an embodiment of the present disclosure, the specific antigen is a polypeptide sequence obtained by analyzing a molecular sequence of RELT and selectively designing according to a structure, antigenicity, hydrophilicity and hydrophobicity of constituent amino acids, and a secondary structure of an RELT protein molecule on a cell membrane. Design results are shown in FIG. 4.

Before the lymphocyte is immunized, a polypeptide with an amino acid sequence set forth in SEQ ID NO: 1 is first synthesized artificially, and then the synthesized polypeptide is used as a raw material for the specific antigen for immunization. When the lymphocyte is immunized, the polypeptide is prepared into a complete antigen through coupling with a carrier protein KLH or OVA, and the complete antigen is used as an immunogen to immunize an animal model.

Based on a general invention concept, an embodiment of the present disclosure also provides a coding gene, including a genome encoding the anti-RELT recombinant monoclonal antibody, where the genome includes a first gene fragment encoding the heavy chain variable region and a second gene fragment encoding the light chain variable region; and a nucleotide sequence of the first gene fragment is set forth in SEQ ID NO: 2 and a nucleotide sequence of the second gene fragment is set forth in SEQ ID NO: 3.

In an embodiment of the present disclosure, on the basis of the anti-RELT recombinant monoclonal antibody designed, the first gene fragment encoding the heavy chain variable region and the second gene fragment encoding the light chain variable region are further introduced, such that the coding gene can be selectively used in an actual production process to directly translate and express the amino acid sequence of the heavy chain variable region set forth in SEQ ID NO: 4 and the amino acid sequence of the light chain variable region set forth in SEQ ID NO: 5 to obtain the complete anti-RELT recombinant monoclonal antibody.

The coding gene is obtained based on the monoclonal antibody described above, and specific composition and sequence information of the monoclonal antibody can refer to the above embodiments. Because the coding gene adopts a part or all of the technical solutions of the above embodiments, the coding gene has at least all beneficial effects brought by the technical solutions of the above embodiments, which will not be repeated here.

Based on a general invention concept, an embodiment of the present disclosure also provides a nucleic acid including the coding gene described above.

The nucleic acid is obtained based on the coding gene described above, and specific sequence information of the coding gene can refer to the above embodiments. Because the nucleic acid adopts a part or all of the technical solutions of the above embodiments, the nucleic acid has at least all beneficial effects brought by the technical solutions of the above embodiments, which will not be repeated here.

Based on a general invention concept, an embodiment of the present disclosure also provides a recombinant expression vector including the nucleic acid described above, where the recombinant expression vector includes a recombinant plasmid.

The recombinant expression vector is obtained based on the nucleic acid described above, and specific sequence information of the nucleic acid can refer to the above embodiments. Because the recombinant expression vector adopts a part or all of the technical solutions of the above embodiments, the recombinant expression vector has at least all beneficial effects brought by the technical solutions of the above embodiments, which will not be repeated here.

Figure 2:
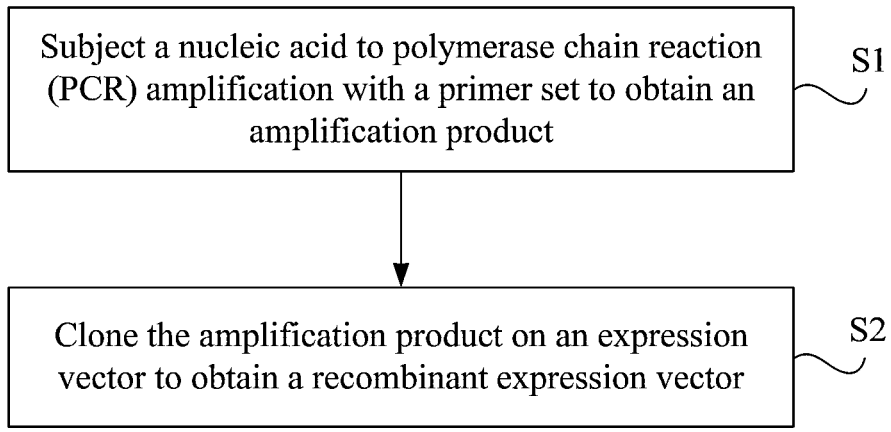
FIG. 2 is a schematic flow chart of a method for preparing a recombinant expression vector provided in an embodiment of the present disclosure.
Figure 3:
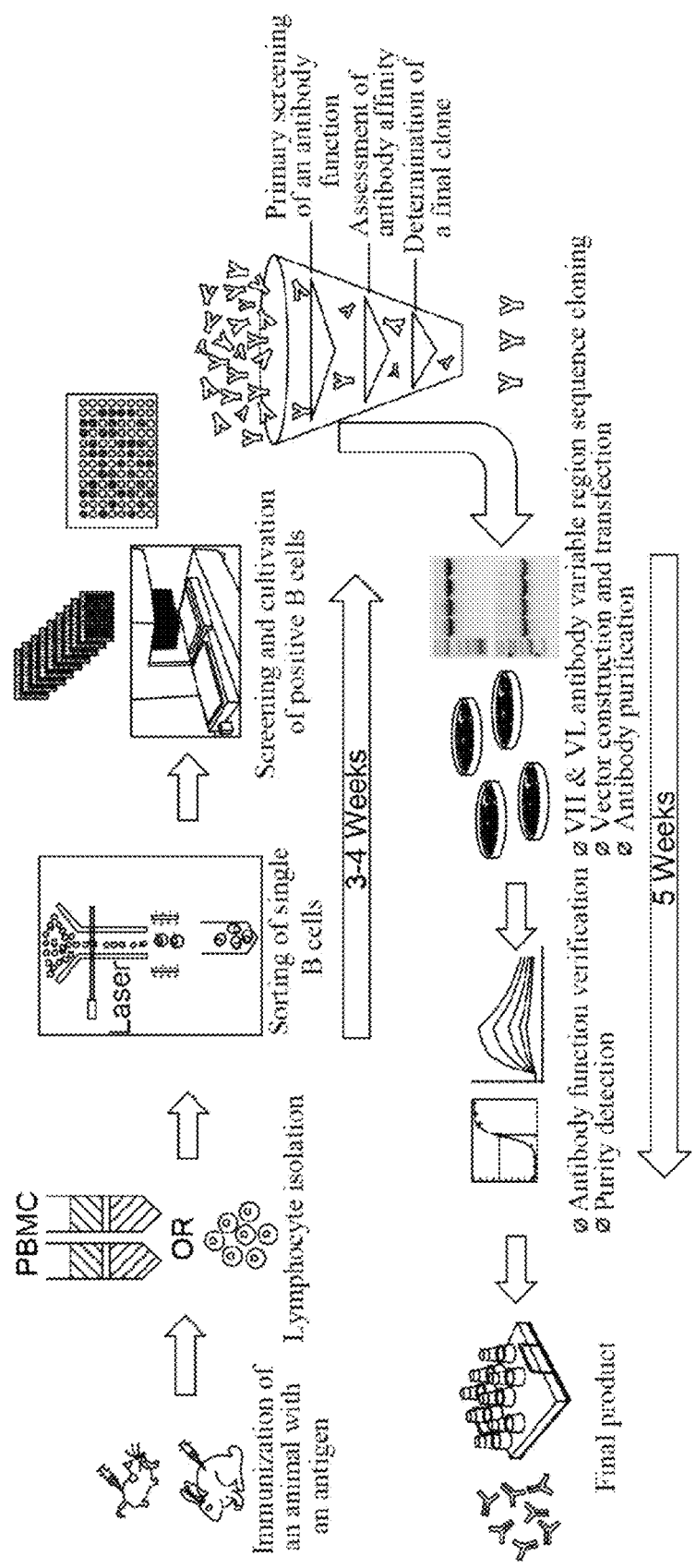
FIG. 3 is a schematic flow chart of a method for preparing an anti-RELT recombinant monoclonal antibody using a rabbit provided in an embodiment of the present disclosure.

As shown in FIG. 2, based on a general invention concept, an embodiment of the present disclosure also provides a method for preparing the recombinant expression vector described above, including:

S1. the nucleic acid described above is subjected to PCR amplification with a primer set to obtain an amplification product; and S2. the amplification product is cloned on an expression vector to obtain the recombinant expression vector, where the primer set includes a primer pair for the heavy chain variable region and a primer pair for the light chain variable region.

The method is a method for preparing the recombinant expression vector, and specific composition and sequence information of the recombinant expression vector can refer to the above embodiments. Because the method adopts a part or all of the technical solutions of the above embodiments, the method has at least all beneficial effects brought by the technical solutions of the above embodiments, which will not be repeated here.

As shown in FIG. 1, based on a general invention idea, an embodiment of the present disclosure provides a method for preparing the anti-RELT recombinant monoclonal antibody, including:

S1. a cell is transfected with the recombinant expression vector described above and then cultivated to obtain a cell culture; and S2. a supernatant of the cell culture is collected and subjected to purification to obtain the anti-RELT recombinant monoclonal antibody.

The method is a method for preparing the anti-RELT recombinant monoclonal antibody, and specific composition and sequence information of the recombinant expression vector can refer to the above embodiments. Because the method adopts a part or all of the technical solutions of the above embodiments, the method has at least all beneficial effects brought by the technical solutions of the above embodiments, which will not be repeated here.

It should be noted that a specific process of the preparation method is as follows:

(1) Rabbit immunization: A molecular sequence of RELT is first analyzed (including analysis of specificity and conservatism of the amino acid sequence, analysis of expressibility of the protein, and analysis of antigenicity of the protein); according to a structure, antigenicity, hydrophilicity and hydrophobicity of constituent amino acids, and a secondary structure of RELT on a cell membrane, a polypeptide sequence of 32 aa to 169 aa is selected as an immunogen and coupled with KLH or OVA to prepare an complete antigen; and a rabbit is immunized with the complete antigen. The polypeptide sequence is an amino acid sequence set forth in SEQ ID NO: 1, and is artificially synthesized.

(2) Antigen-specific B cell screening: A peripheral blood sample is collected from an immunized rabbit, peripheral blood B cells are isolated from the peripheral blood sample, positive B cells are sorted from the peripheral blood B cells to obtain single positive B lymphocytes that can efficiently secrete a corresponding antibody, and total RNA is extracted from the single positive B lymphocytes.

(3) Antibody sequence acquisition: PCR amplification is conducted with a specific primer set to obtain a nucleotide sequence set forth in SEQ ID NO: 2 for a heavy chain variable region of the antibody and a nucleotide sequence set forth in SEQ ID NO: 3 for a light chain variable region of the antibody. The primer set includes a primer pair for the heavy chain variable region and a primer pair for the light chain variable region; an upstream primer of the primer pair for the heavy chain variable region is set forth in SEQ ID NO: 6, and a downstream primer of the primer pair for the heavy chain variable region is set forth in SEQ ID NO: 7; and an upstream primer of the primer pair for the light chain variable region is set forth in SEQ ID NO: 8, and a downstream primer of the primer pair for the light chain variable region is set forth in SEQ ID NO: 9.

(4) Antibody expression and purification: The nucleotide sequences obtained above are cloned into an expression vector, a transfection reagent is used to transiently transfect a cultivated HEK293F cell with the expression vector, and a resulting cell supernatant is collected after the culture and amplification of the cell, and subjected to purification with Protein A to obtain the anti-RELT recombinant monoclonal antibody with a purity of higher than 95%.

Based on a general invention concept, an embodiment of the present disclosure also provides an RELT protein detection device, where a biological component of the detection device includes at least one selected from the group consisting of the anti-RELT recombinant monoclonal antibody, the coding gene, the nucleic acid, and the recombinant expression vector, and the detection device includes at least one selected from the group consisting of a test kit, an antibody chip, and an antibody probe.

The RELT protein detection device is based on the anti-RELT monoclonal antibody, the coding gene, the nucleic acid, or the recombinant expression vector, and specific sequence information of the anti-RELT monoclonal antibody, the coding gene, the nucleic acid, or the recombinant expression vector can refer to the above embodiments. Because the RELT protein detection device adopts a part or all of the technical solutions of the above embodiments, the RELT protein detection device has at least all beneficial effects brought by the technical solutions of the above embodiments, which will not be repeated here.

Based on a general invention concept, an embodiment of the present disclosure also provides a use of an anti-RELT recombinant monoclonal antibody, including a use of the anti-RELT recombinant monoclonal antibody in preparation of a therapeutic drug for an autoimmune disease.

The autoimmune disease includes at least one selected from the group consisting of type 1 diabetes, rheumatoid arthritis, systemic lupus erythematosus, Sjogren's syndrome, multiple sclerosis, Hashimoto's thyroiditis, primary myxedema, hyperthyroidism, autoimmune hemolytic anemia, ulcerative colitis, atrophic gastritis, and autoimmune glomerulonephritis.

The use is implemented based on the anti-RELT recombinant monoclonal antibody described above, and specific sequence information and a composition of the anti-RELT recombinant monoclonal antibody can refer to the above embodiments. Because the use adopts a part or all of the technical solutions of the above embodiments, the use has at least all beneficial effects brought by the technical solutions of the above embodiments, which will not be repeated here.

The present disclosure will be further described below in conjunction with specific examples. It should be understood that these examples are merely intended to describe the present disclosure, rather than to limit the scope of the present disclosure. Experimental methods which are not specified with specific conditions in the following examples are usually conducted in accordance with national standards. If there are no corresponding national standards, a method should be conducted in accordance with common international standards, conventional conditions, or conditions recommended by a manufacturer.

Laboratory animals used in the examples are treated according to "*Implementation Rules for Management of Medical Laboratory Animals*", and laboratory animals such as NOD mice, C57BL/6 mice, and NOD-SCID mice all are maintained in SPF-grade animal facilities.

Example 1

Preparation and Screening Process of an Anti-RELT Recombinant Monoclonal Antibody:

(1) Preparation of an Antigen:

A molecular sequence of RELT was analyzed, and a selective design was conducted according to a structure, antigenicity, hydrophilicity and hydrophobicity of constituent amino acids, and a secondary structure of an RELT protein molecule on a cell membrane. Results were shown in FIG. 4. According to the results shown in FIG. 4, a peptide of 32 aa to 169 aa was selected as a polypeptide for synthesizing an immunizing antigen. A sequence of the polypeptide was as follows:

```
                                          (SEQ ID NO: 1)
PTPITPWLCPPGKEPDPDPGQGTLCRTCPPGTFSASWNSYPCQPHYRCS

LQKRLEAQAGTATHDTMCGDCQHGWFGPQGVPHVPCQPCSKAPPSTGGC

DESGRRGRRGVEVAAGTSSNGEPRQPGNGTRAGGPEETAA
```

The polypeptide was coupled with a protein KLH or OVA to prepare a complete antigen as an immunogen for immunization of a rabbit.

(2) Immunization of an Animal with the Complete Antigen:

The complete antigen including the polypeptide sequence set forth in SEQ ID NO: 1 (RELT antigen) was mixed with complete Freund's adjuvant to obtain a first mixture, and the first mixture was emulsified and then subcutaneously injected into a plurality of New Zealand white rabbits for first immunization. Two weeks later, the RELT antigen was mixed with incomplete Freund's adjuvant to obtain a second mixture, and the second mixture was emulsified and then used for second immunization.

Figure 5:
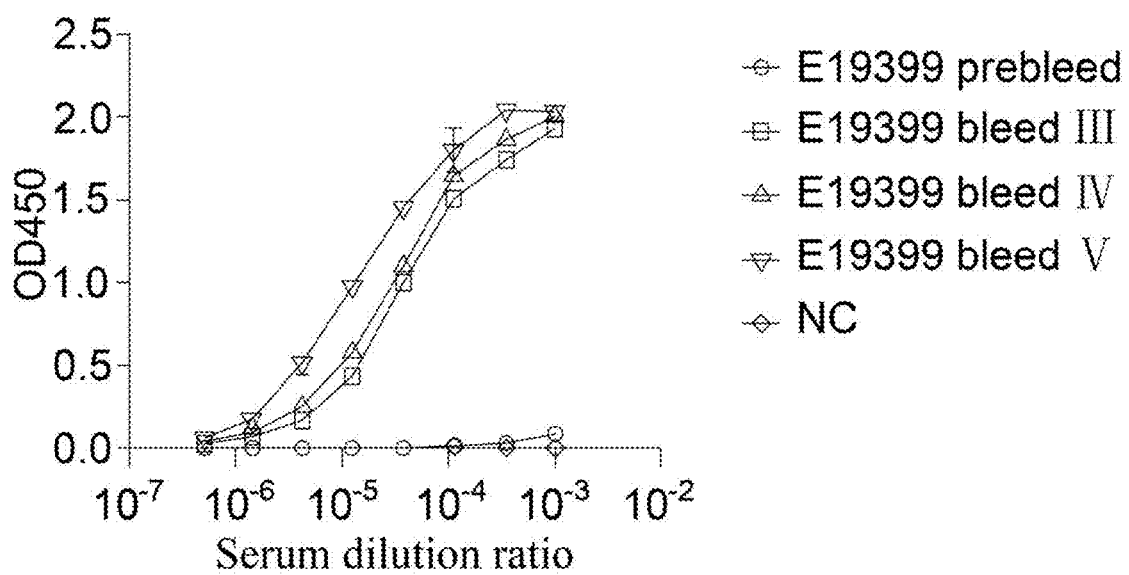
FIG. 5 is a statistical graph of enzyme-linked immunosorbent assay (ELISA) results of serum titers of different rabbits immunized three times provided in an embodiment of the present disclosure.

Four weeks later, third immunization was conducted. After the third immunization, blood was collected, and serially diluted and tested by an ELISA method for a serum titer. Results were shown in FIG. 5.

One week later, a rabbit (E19399) with a maximum titer of an immune antibody of RELT antigen was selected and subjected to fourth immunization. 1 week later, the rabbit was subjected to fifth immunization. In this way, a standard 63 d immunization process was completed to allow the next isolation of positive single B cells.

(3) Isolation of Single B Cells:

After the fifth immunization was completed, a rabbit was euthanized, a spleen was isolated, cut by surgical scissors into pieces, and then filtered through a 70 m filter mesh, and red blood cells were lysed to obtain a spleen single-cell suspension. Flow cytometry antibodies (CD3-PE, CD4-PE, CD8-PE, CD11B-PE, CD11C-PE, MHCII-PE, and CD19-APC) and biotin were used for labeling to obtain RELT-biotin-FITC, and then flow cytometry was used to sort out positive B cells lin (CD3, CD4, CD8, CD11B, CD11C, MHCII)$^-$CD19$^+$RELT-biotin$^+$ capable of specifically recognizing the antigen and then sort out single B cell positive clones capable of specifically recognizing the antigen.

(4) Screening of the Optimal Positive B Cell Clones:

1,000 single B lymphocyte clones (enriched by the antigen) were sorted out and cultured. Each B lymphocyte positive clone was cultivated separately for 3 d to 5 d in an incubator at 37° C. and 5% $CO_2$, then a cell suspension was collected and centrifuged to obtain a supernatant, and the supernatant was detected by ELISA. A positive B clone with the optimal titer for specific recognition of the antigen was screened out, and denoted as E19399-5B2.

(5) Cloning of an Antibody Sequence of the Lymphocyte E19399-5B2:

Total RNA was extracted from the positive B lymphocyte E19399-5B2, and reverse-transcribed into cDNA according to instructions of a TaKaRa reverse-transcription kit: PrimeScript™ RT reagent Kit (Perfect Real Time). A specific primer set (a primer pair for a heavy chain variable region: VH-F: AGACTGGGCTGCGCTGGCTTC(SEQ ID NO:6), and VH-R: GTGAGGGTGCCCGAG(SEQ ID NO:7); and a primer pair for a light chain variable region: VK-F: ATGGACAYGAGGGCCCCCACTC(SEQ ID NO:8), and VK-R: GGTGGGAAGATGAGGACAGTAGG(SEQ ID NO:9)) was used to amplify antibody sequences, then gene sequencing was conducted to obtain nucleotide sequences for the heavy chain variable region and the light chain variable region of the antibody, and then the nucleotide sequences for the heavy chain variable region and the light chain variable region of the antibody were cloned into a eukaryotic expression vector pCDNA3.4, such that an antibody cloning work was completed to allow the subsequent cell transfection.

(6) Transfection of Cells and Preparation and Purification of a Monoclonal Antibody:

Transfection of suspended HEK293F cells: An HEK293F cell to be transfected was prepared in advance, collected through centrifugation, resuspended with a fresh medium, and added to a 24-well plate at 1.5 mL/well with a density of 3*10$^6$ cells/mL according to a required quantity.

Figure 6:
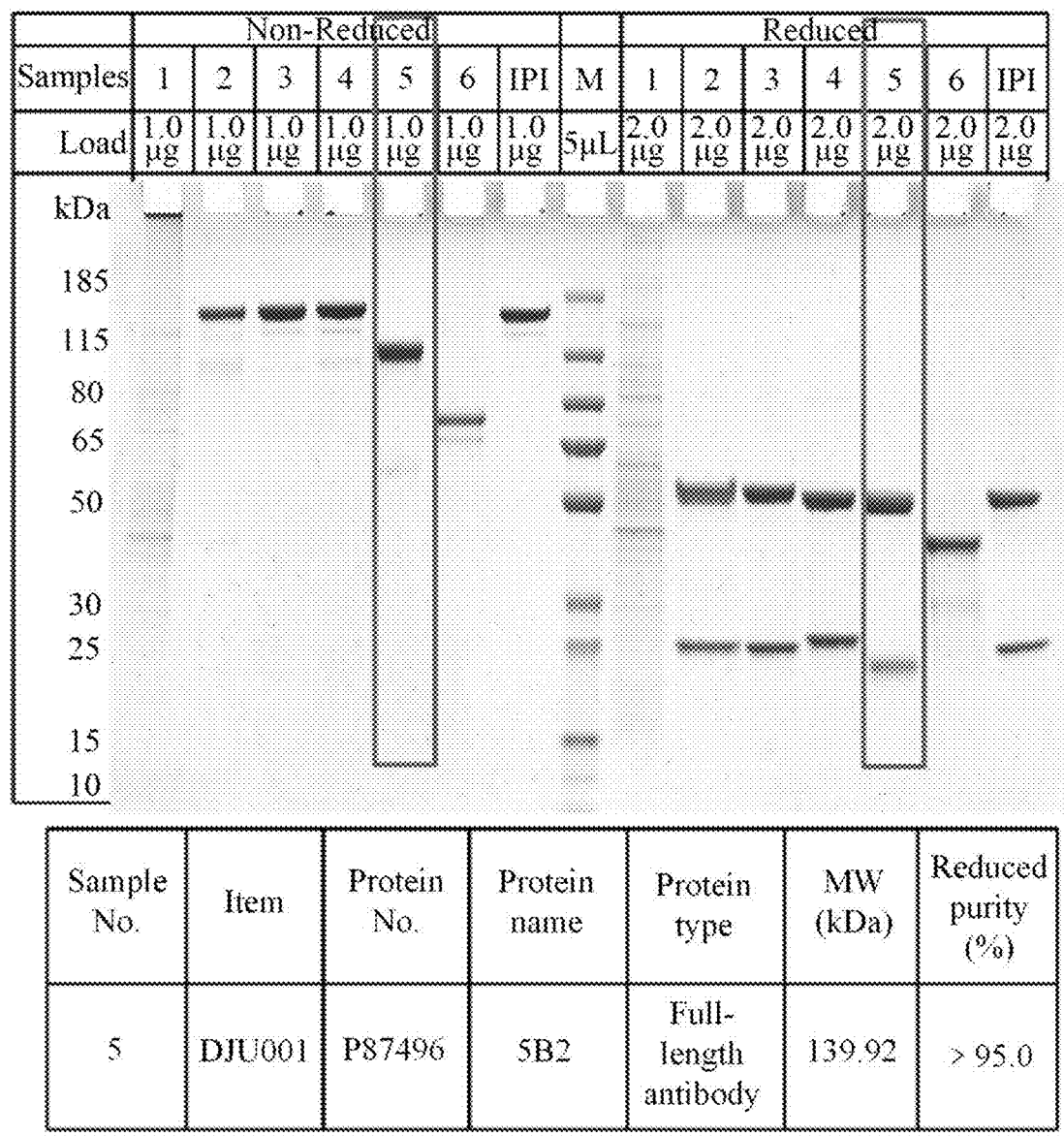
FIG. 6 is a sketch map of purity detection results of an anti-RELT recombinant monoclonal antibody provided in an embodiment of the present disclosure.

A prepared pCDNA3.4 eukaryotic expression vector was mixed with PEI in a ratio of 1:6 to obtain a mixture, then the mixture was added to the prepared HEK293F cell, and the cell was cultivated in a shaker at 37° C. and 5% $CO_2$ for 3 d to 5 d; and a resulting cell suspension was collected and centrifuged to obtain a supernatant, and the supernatant was subjected to purification with Protein A to obtain an antibody with a purity of higher than 95%. Detection results were shown in FIG. 6. A purified monoclonal antibody was tested for a concentration, dispensed, and stored in a refrigerator at 4° C. to 8° C.

Finally, an amino acid sequence of a heavy chain variable region of an anti-RELT recombinant rabbit monoclonal antibody E19399-5B2 was encoded by a DNA sequence set forth in SEQ ID NO: 2, and an amino acid sequence of a light chain variable region of the anti-RELT recombinant rabbit monoclonal antibody was encoded by a DNA sequence set forth in SEQ ID NO: 3. Specific sequences were as follows:

(SEQ ID NO: 2)
ATGGAGACTGGGCTGCGCTGGCTTCTCCTGGTCGCTGTACTCAGAGGTG

TCCAGTGTCAGTCGGTGAAGGAGTCCGGGGGAGGCCTCTTCAAGCCAAC

GGATACCCTGACACTCACCTGCACAGTCTCTGGATTCTCCCTCAGTACC

TATGCAATGTCCTGGGTCCGCCAGACTCCAGGGATTGGGCTGGAGTGGA

TCGGGATCGTTAATGTTGCTGGTGATACAGCCTACGCGAGCTGGGCGAT

GAGCCGATCCACCATCACCAGAAACACCAACGACAACACGGTGACTCTG

AAAATGACCAGTCTGACAGCCGCGGACACGGCCACCTATTTCTGTACAC

GACATGGTGAGAATATTGGTGACATGTGGGGCCCAGGCACCCTGATTGC

CGTCTCCTCAGTGCCTGCAACCCCCCGATCATCTTCCCGCTGACCTGC

CCCGGGTGTGTACTGAAAGACACTTCAGCGACCATTGTCGCCGGCTGCC

TGGTCAAAGGCTACCTCCCGGAGCCAGTGACCGTGACCTGGAACTCGGG

CACCCTCACCAATGGGGTACGCACCTTCCCGTCCGTCCGGCAGTCCTCA

GGCCTCTACTCGCTGAGCAGCGTGGTGAGCGTGACCTCAAGCAGCCAGC

CCGTCACCTGCAACGTGGCCCACCCAGCCACCAACACCAAAGTGGACAA

GACCGTTGCGCCCTCGACATGCAGCAAGCCCATGTGCCCACCCCCTGAA

CTCCCGGGGGGACCGTCTGTCTTCATCTTCCCCCCAAAACCCAAGGACA

CCCTCATGATCTCACGCACCCCCGAGGTCACATGCGTGGTGGTGGACGT

GAGCCAGGATGACCCCGAGGTGCAGTTCACATGGTACATAAACAACGAG

CAGGTGCGCACCGCCCGGCCGCCGCTACGGGAGCAGCAGTTCAACAGCA

CGATCCGCGTGGTCAGCACCCTCCCCATCGCGCACCAGGACTGGCTGAG

GGGCAAGGAGTTCAAGTGCAAAGTCCACAACAAGGCACTCCCGGCCCCC

ATCGAGAAAACCATCTCCAAAGCCAGAGGGCAGCCCCTGGAGCCGAAGG

TCTACACCATGGGCCCTCCCCGGGAGGAGCTGAGCAGCAGGTCGGTCAG

CCTGACCTGCATGATCAACGGCTTCTACCCTTCCGACATCTCGGTGGAG

TGGGAGAAGAACGGGAAGGCAGAGGACAACTACAAGACCACGCCGACCG

TGCTGGACAGCGACGGCTCCTACTTCCTCTACAGCAAGCTCTCAGTGCC

CACGAGTGAGTGGCAGCGGGGCGACGTCTTCACCTGCTCCGTGATGCAC

GAGGCCTTGCACAACCACTACACGCAGAAGTCCATCTCCCGCTCTCCGG

GTAAATAG.

(SEQ ID NO: 3)
ATGGACACGAGGGCCCCCACTCAGCTGCTGGGGCTCCTGCTGCTCTGGC

TCCCAGGTGCCATCTGTGACCCTGTGATGACCCAGACTCCATCTTCCAC

GTCTGCGGCTGTGGGAGGCACAGTCACCATCAATTGCCAGGCCAGTCAG

```
-continued
AGTGTTTATGCTAACAACTACTTATCCTGGTTTCAGAAGAAACCAGGAC

AGCCTCCCAAGCAACTGATCTATGATGCATCCACTCTGGCATCTGGGGT

CCCATCGCGGTTCAAAGGCAGTGGATCTGGGACACAGTTCACTCTCACC

ATCAGCGGCGTGCAGTGTGACGATGCTGCCGCCTACTATTGTGCAGGCG

GTTTTACTGGTGCGATTTTTCCTTTCGGCGGAGGGACCGAGGTGGTGGT

CAAAGGTGATCCAGTTGCACCTACTGTCCTCATCTTCCCACCAGCTGCT

GATCAGGTGGCAACTGGAACAGTCACCATCGTGTGTGTGGCGAATAAAT

ACTTTCCCGATGTCACCGTCACCTGGGAGGTGGATGGCACCACCCAAAC

AACTGGCATCGAGAACAGTAAAACACCGCAGAATTCTGCAGATTGTACC

TACAACCTCAGCAGCACTCTGACACTGACCAGCACACAGTACAACAGCC

ACAAAGAGTACACCTGCAAGGTGACCCAGGGCACGACCTCAGTCGTCCA

GAGCTTCAATAGGGGTGACTGTTAG.
```

The two base sequences obtained were translated into corresponding amino acid sequences. An amino acid sequence of the heavy chain variable region of the anti-RELT recombinant monoclonal antibody E19399-5B2 was set forth in SEQ ID NO: 4, and an amino acid sequence of the light chain variable region of the anti-RELT recombinant monoclonal antibody E19399-5B2 was set forth in SEQ ID NO: 5:

```
                                            (SEQ ID NO: 4)
METGLRWLLLVAVLRGVQCQSVKESGGGLFKPTDTLTLTCTVSGFSLST

YAMSWVRQTPGIGLEWIGIVNVAGDTAYASWAMSRSTITRNTNDNTVTL

KMTSLTAADTATYFCTRHGENIGDMWGPGTLIAVSSVPATPPIIFPLTC

PGCVLKDTSATIVAGCLVKGYLPEPVTVTWNSGTLTNGVRTFPSVRQSS

GLYSLSSVVSVTSSSQPVTCNVAHPATNTKVDKTVAPSTCSKPMCPPPE

LPGGPSVFIFPPKPKDTLMISRTPEVTCVVVDVSQDDPEVQFTWYINNE

QVRTARPPLREQQFNSTIRVVSTLPIAHQDWLRGKEFKCKVHNKALPAP

IEKTISKARGQPLEPKVYTMGPPREELSSRSVSLTCMINGFYPSDISVE

WEKNGKAEDNYKTTPTVLDSDGSYFLYSKLSVPTSEWQRGDVFTCSVMH

EALHNHYTQKSISRSPGK*.

(SEQ ID NO: 5)
MDTRAPTQLLGLLLLWLPGAICDPVMTQTPSSTSAAVGGTVTINCQASQ

SVYANNYLSWFQKKPGQPPKQLIYDASTLASGVPSRFKGSGSGTQFTLT

ISGVQCDDAAAYYCAGGFTGAIFPFGGGTEVVVKGDPVAPTVLIFPPAA

DQVATGTVTIVCVANKYFPDVTVTWEVDG*.
```

Example 2

On the basis of the anti-RELT recombinant monoclonal antibody E19399-5B2 obtained in Example 1, the subsequent experiment was conducted.

The anti-RELT recombinant monoclonal antibody was used as a primary antibody and detected by WB, specifically including:
(1) A total protein was extracted from mouse CD4+ cells, 20 μL of a total protein solution was taken and subjected to electrophoresis with an 8% gel at a constant voltage of 80 V, and after marker separation, the voltage was adjusted to 110 V until proteins with different molecular weights were fully separated.
(2) Membrane transfer: A membrane transfer solution (200 mL of methanol, 5.8 g of Tris, and 2.9 g of Gly were diluted with double distilled water to 1,000 mL) was prepared and pre-cooled in a 4° C. refrigerator; fixed membrane transfer clamps were placed in a membrane transfer tank, the membrane transfer tank was fully filled with the membrane transfer solution, and finally the membrane transfer tank was placed in a foam box fully filled with ice; and membrane transfer was conducted at a constant flow of 180 mA for 2.5 h.
(3) Blocking: 5% milk was prepared with TBST to allow blocking for 1 h or overnight at 4° C.
(4) Primary antibody incubation: After the blocking was completed, a membrane was quickly washed 3 times with TBST. The anti-RELT recombinant monoclonal antibody E19399-5B2 was diluted to 0.5 μg/mL, and then a blocked membrane was placed in a corresponding diluted antibody and incubated overnight in a 4° C. shaker.
(5) A membrane was taken out and washed in a TBST solution 5 times (5×10 min).
(6) Secondary antibody incubation: HRP-anti-rabbit IgG was diluted with TBST at 1:5,000, thoroughly mixed, added to a membrane strip, and incubated at room temperature for 1 h.
(7) A membrane strip was taken out and washed in a TBST solution 5 times (5×10 min).
(8) ECL and AB solutions (0.5 mL of each solution) were mixed at 1:1 and evenly poured on a PVDF membrane and incubated for 2 min.
(9) Exposure: A chromogenic cassette was moistened and wipe-dried with clean toilet paper, a membrane was spread in the chromogenic cassette, air bubbles were removed, a negative was placed in the chromogenic cassette, and an X-ray film was exposed for different time periods according to fluorescence intensities.
(10) Exposure: A film was placed in a developing solution for 1 min to 3 min, rinsed with clear water, then placed in a fixing solution for about 9 min, and finally oven-dried in an oven at 65° C., and then a target band was determined according to a marker. Results were analyzed. The results were shown in FIG. 7.

Figure 7:
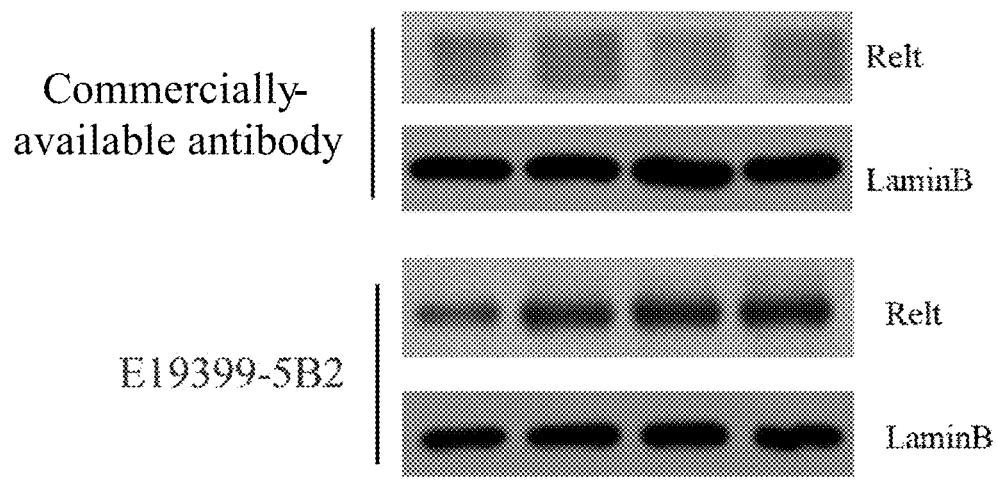
FIG. 7 is a comparison diagram of western blotting (WB) detection indexes of an anti-RELT recombinant monoclonal antibody provided in an embodiment of the present disclosure and a commercially-available anti-RELT antibody.

A band size in FIG. 7 is 43 kDa. It can be seen from this figure that the anti-RELT recombinant monoclonal antibody E19399-5B2 can specifically recognize RELT protein with a molecular weight of about 43 kDa in a CD4+ T cell lysate in a lane, indicating that the anti-RELT recombinant monoclonal antibody E19399-5B2 in the present disclosure can recognize RELT protein with high specificity, and exhibits significantly-better binding specificity than a commercially-available antibody.

Example 3

On the basis of the anti-RELT recombinant monoclonal antibody E19399-5B2 obtained in Example 1, the subsequent experiment was conducted.

The anti-RELT recombinant monoclonal antibody E19399-5B2 was used as a primary antibody and detected by immunofluorescence assay, specifically including:
(1) Preparation of sample sections: A mouse pancreas fixed with 10% neutral formaldehyde and embedded with paraffin was sectioned, then baked in a 60° C. incubator for 1 h to 2 h, and then stored for later use.

(2) Section dewaxing: After paraffin on a tissue was fully dissolved, a slide was dewaxed in first xylene (15 min), second xylene (15 min), third xylene (10 min), first absolute ethanol (5 min), second absolute ethanol (5 min), first 95% ethanol (5 min), second 95% ethanol (5 min), and 80% ethanol (5 min) successively and then rinsed with running water (tap water) for 2 min to complete the dewaxing.

(3) Antigen retrieval: A high-temperature thermal retrieval method was recommended. A slide was placed in an elution box with a sodium citrate retrieval solution (a weakly-acidic solution, which was prepared just before use), then the elution box was placed in a pressure cooker, and the sodium citrate retrieval solution was heated and boiled for 5 min. The antigen retrieval was conducted because aldehyde fixation would cause protein crosslinking to mask epitopes and weaken a staining signal.

(4) Autofluorescence quenching: The slide was added with an autofluorescence quenching agent solution A, and then incubated for 30 min and then washed with double distilled water for 5 min; and then an autofluorescence quenching agent solution B was added to the section, and the section was incubated for 5 min, then washed with double distilled water for 5 min, and rinsed once with PBST.

(5) Blocking: A blocking solution (100 μL of 10% BSA+ 50 μL of donkey serum+850 μL of PBS) was added to allow blocking at room temperature for 1 h, and after the blocking was completed, the blocking solution was directly shaken off without washing.

(6) Primary antibody incubation: A tissue was circled with a histochemical pen in a sample zone of a slide, 100 μL of a 10 ng/mL anti-RELT recombinant monoclonal antibody E19399-5B2 was added to completely cover the tissue, and the tissue was incubated in a 37° C. incubator for 1 h and then rinsed with PBST 3 times for 5 min each time.

(7) Secondary antibody incubation: A secondary antibody diluted at a dilution factor of 1:200 to 1:400 (a diluent for the secondary antibody was the blocking solution 10-fold diluted) was used to incubate the tissue at room temperature for 1 h, rinsed with PBST 3 times for 5 min each time, and then rinsed once with purified water.

(8) Nucleus staining: A tissue was immersed in DAPI for 2 min to 5 min (which should not be too long) to allow the nucleus staining, and then washed with 1×PBS 3 times for 5 min each time.

(9) Mounting: An anti-fluorescence quenching agent was added to a sample for mounting, and the sample was observed under a fluorescence microscope. Results were shown in FIG. 8.

Figure 8:
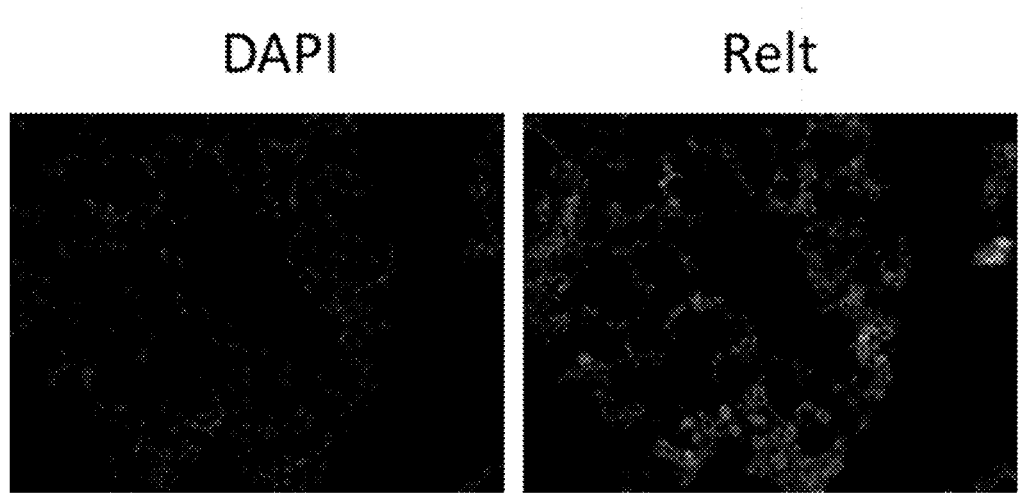
FIG. 8 is a sketch map of immunofluorescence assay results of an anti-RELT recombinant monoclonal antibody provided in an embodiment of the present disclosure.

According to the results in FIG. 8, RELT has a green fluorescence signal in a mouse pancreatic tissue, indicating that the anti-RELT recombinant monoclonal antibody E19399-5B2 in the present disclosure has excellent specificity and a strong positive signal and thus can be used for immunofluorescence staining.

Example 4

On the basis of the anti-RELT recombinant monoclonal antibody E19399-5B2 obtained in Example 1, the subsequent experiment was conducted.

A neutralizing function of the anti-RELT recombinant monoclonal antibody was verified by a cell experiment, specifically including:

(1) A culture plate was coated with anti-αCD3 (5 μg/mL)+ anti-αCD28 (5 μg/mL) 12 h in advance.

(2) T cell sorting: A B6 background mouse was euthanized and soaked in an alcohol for 5 min, and a spleen was collected and placed in 1640 (in a small dish); a 70 μm filter mesh was taken and placed on a 50 mL centrifuge tube; a thruster of a 1 mL syringe was taken; the spleen was placed on the filter mesh, and a small amount of 1640 was added to rinse the filter mesh and the spleen; the spleen was ground with the thruster, during which 1640 was continuously added to fully grind the spleen into a single-cell suspension; and red blood cells were lysed to prepare single-cell suspension, and T cells were sorted out by naive kit magnetic beads.

(3) The sorted naive T cells were inoculated in an anti-αCD3/αCD28-coated culture plate and cultivated for 12 h. In one group, 10 μL of the anti-RELT recombinant monoclonal antibody E19399-5B2 was added; and the other group was set as a control. The expression of T cell activation markers CD25 and CD69 was detected. Results were shown in FIG. 9. It can be seen that the addition of the anti-RELT recombinant monoclonal antibody E19399-5B2 can significantly inhibit the activation of T cells.

(4) The sorted naive T cells were inoculated in an anti-αCD3/αCD28-coated culture plate, then IL-2 (10 ng/mL) and IL-12 (10 ng/mL) were added, and the T cells were cultivated for 72 h. In one group, 10 μL of the anti-RELT recombinant monoclonal antibody E19399-5B2 was added; and the other group was set as a control. The differentiation of T cell subsets was detected.

Figure 9:
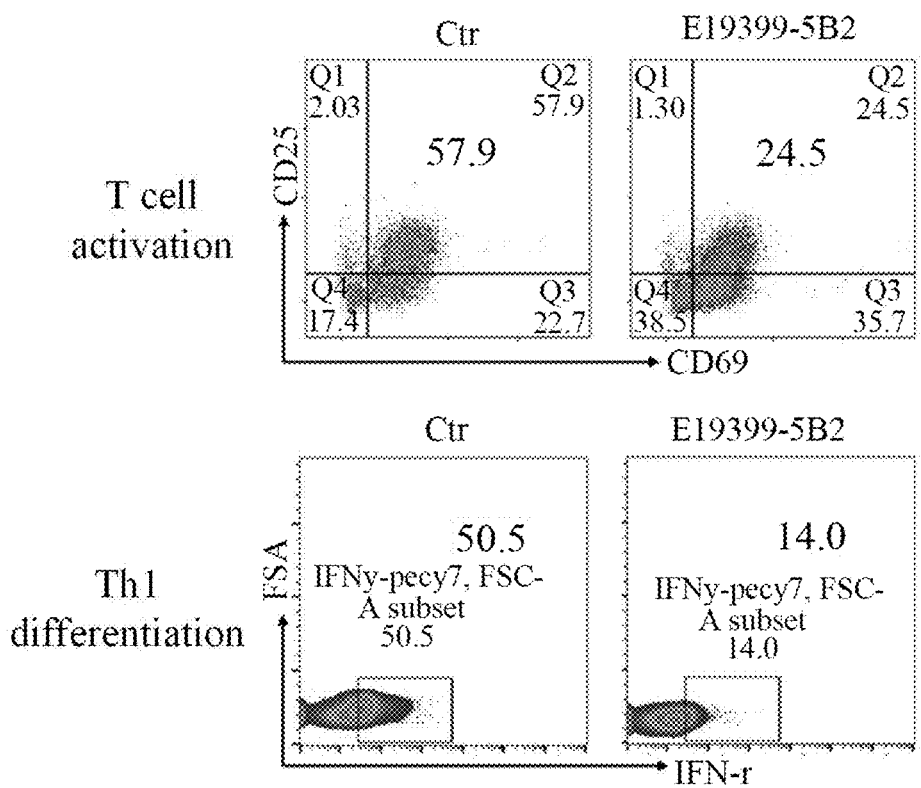
FIG. 9 is a sketch map of impacts of an anti-RELT recombinant monoclonal antibody provided in an embodiment of the present disclosure on activation and differentiation of T cells.

Results were shown in FIG. 9. It can be seen that the addition of the anti-RELT recombinant monoclonal antibody E19399-5B2 can significantly inhibit the differentiation of Th1 cell subsets.

Example 5

On the basis of the anti-RELT recombinant monoclonal antibody E19399-5B2 obtained in Example 1, the subsequent experiment was conducted.

A neutralizing function of the anti-RELT recombinant monoclonal antibody was verified by an animal model experiment, specifically including:

(1) 8-week-old NOD mice each were intraperitoneally injected with the anti-RELT recombinant monoclonal antibody E19399-5B2 (n=15) or a control IgG (n=15) (10 mg per kg of a body weight, and about 100 μg per mouse) three times a week consecutively for two weeks in total, and then the administration was stopped.

(2) After the administration was stopped, a blood glucose level was monitored every week. When two consecutive blood glucose levels exceeded 12.8 mM, it was considered as the onset of type 1 diabetes. When an incidence reached 80% in one group, the experiment was terminated.

(3) In a control group, the onset began in mice at an age of 14 weeks, and an incidence reached 80% in mice at an age of 30 weeks. In the anti-RELT recombinant monoclonal antibody E19399-5B2 treatment group, the onset began in mice at an age of 18 weeks, an onset time was delayed, and an incidence was only 45% in mice at an age of 30 weeks, indicating that the anti-RELT recombinant monoclonal antibody E19399-5B2 has an effect on inhibition of spontaneous diabetes in NOD mice. Results were shown in FIG. 10.

Figure 10:
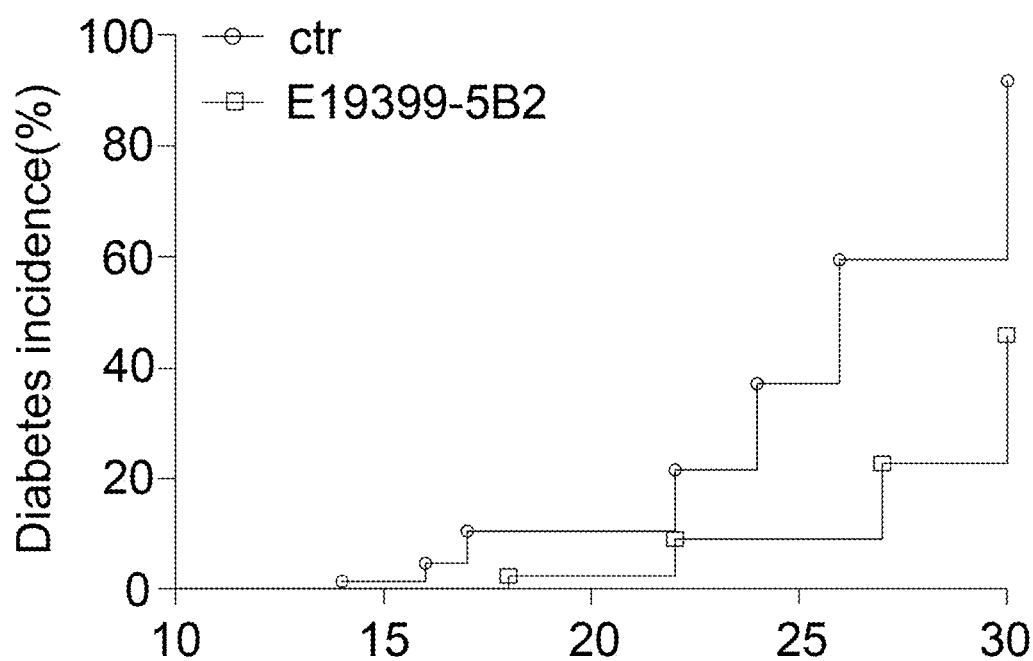
FIG. 10 shows the mitigation of an anti-RELT recombinant monoclonal antibody provided in an embodiment of the present disclosure for a spontaneous diabetes progression in NOD mice.

Since the anti-RELT recombinant monoclonal antibody E19399-5B2 has a biological activity of neutralizing RELT, results of a cell experiment in FIG. 10 show that the E19399-5B2 antibody can significantly inhibit a functional activity of RELT. In addition, results of a mouse animal experiment prove that the E19399-5B2 antibody can slow down a progression of an autoimmune disease such as type 1 diabetes by blocking a biological function of RELT and inhibiting the activation and Th1 subset differentiation of T cells.

In summary, the anti-RELT recombinant monoclonal antibody provided in the embodiment of the present disclosure is widely used and can accurately identify the expression of RELT. According to detection results of different manners, the anti-RELT recombinant monoclonal antibody can specifically recognize and bind to an RELT epitope, and can be used in detection and screening fields such as IHC, indirect ELISA, WB, antibody chip preparation, and flow cytometry. It should be emphasized that the anti-RELT recombinant monoclonal antibody has a biological activity of neutralizing RELT, and the results of the mouse animal experiment show that the anti-RELT recombinant monoclonal antibody can significantly inhibit a functional activity of RELT.

The embodiments of the present disclosure also disclose a specific sequence of an RELT antigen required for preparation of the anti-RELT recombinant monoclonal antibody, amino acid sequences of the anti-RELT recombinant monoclonal antibody, nucleotide sequences encoding the anti-RELT recombinant rabbit monoclonal antibody, a recombinant expression vector, a preparation method, and a use of the anti-RELT recombinant monoclonal antibody in an RELT protein detection method or device.

Various embodiments of the present disclosure may exist in a form of a range. It should be understood that the description in a form of a range is merely for convenience and conciseness and should not be construed as a hard limitation on the scope of the present disclosure. Therefore, the description of a range should be considered as specifically disclosing all possible sub-ranges and any single value within this range. For example, the description of a range from 1 to 6 should be considered as specifically disclosing sub-ranges, such as 1 to 3, 1 to 4, 1 to 5, 2 to 4, 2 to 6, and 3 to 6, and any single number in the range, such as 1, 2, 3, 4, 5, and 6, which is applicable regardless of any range. In addition, when a numeric range is mentioned herein, it means that any cited number (fraction or integer) in the range is included.

In the present disclosure, in the absence of a statement to the contrary, an orientation word such as "upper" and "lower" refers specifically to an graph-oriented orientation of a surface in an drawing. In addition, in the description of the present disclosure, terms "including", "comprising", or the like refer to "including, but not limited to". Relational terms herein such as "first" and "second" are merely used to distinguish one entity or operation from another entity or operation without necessarily requiring or implying any actual such relationship or order between such entities or operations. The term "and/or" herein describes an association relationship between associated objects, and indicates three types of relationships. For example, "A and/or B" may indicate that A exists alone, A and B coexist, or B exists alone. "A" and "B" each may be singular or plural. The term "at least one" herein refers to one or more, and the term "a plurality of" refers to two or more. The term "at least one", "at least one of the following items", or a similar expression refers to any combination of these items, including any combination of single items or a plurality of items. For example, "at least one of a, b, or c" or "at least one of a, b, and c" can indicate: a, b, c, a-b (namely, a and b), a-c, b-c, or a-b-c, where a, b, and c may each be in a single or plural form.

The above are only embodiments of the present disclosure, which allows those skilled in the art to understand and implement the present disclosure. Various modifications to the embodiments are readily apparent to a person skilled in the art, and the generic principles defined herein may be practiced in other embodiments without departing from the spirit or scope of the present disclosure. Thus, the present disclosure is not limited to the embodiments shown herein, but falls within the widest scope consistent with the principles and novel features disclosed herein.

What is claimed is:

1. An anti-receptor expressed on lymphoid tissues (RELT) recombinant monoclonal antibody, comprising a heavy chain variable region and a light chain variable region, wherein the amino acid sequence of the heavy chain variable region is set forth in SEQ ID NO: 4; the amino acid sequence of the light chain variable region is set forth in SEQ ID NO: 5; and the anti-RELT recombinant monoclonal antibody has a biological activity of neutralizing a function of RELT.

2. The anti-RELT recombinant monoclonal antibody according to claim 1, wherein the monoclonal antibody is obtained by immunizing a lymphocyte with a specific antigen, and the amino acid sequence of the specific antigen is set forth in SEQ ID NO: 1.

* * * * *